United States Patent [19]

Buckholtz et al.

[11] 4,091,031
[45] * May 23, 1978

[54] PROCESS FOR THE MANUFACTURE OF SUBSTITUTED THIANTHRENE BASED PRODUCTS

[75] Inventors: Harry E. Buckholtz, Kenmore; Arun C. Bose, Tonawanda, both of N.Y.

[73] Assignee: Hooker Chemicals & Plastics Corp., Niagara Falls, N.Y.

[*] Notice: The portion of the term of this patent subsequent to Dec. 14, 1993, has been disclaimed.

[21] Appl. No.: 737,320

[22] Filed: Nov. 1, 1976

Related U.S. Application Data

[63] Continuation-in-part of Ser. No. 521,108, Nov. 5, 1974, Pat. No. 3,997,560.

[51] Int. Cl.$^2$ ............................................. C07D 339/08
[52] U.S. Cl. .................................................. 260/327 P
[58] Field of Search ..................................... 260/327 P

[56] References Cited

U.S. PATENT DOCUMENTS 3,997,560  12/1976  Buckholtz et al. ............... 260/327 P

*Primary Examiner*—Cecilia M. Jaisle
*Attorney, Agent, or Firm*—Peter F. Casella; William J. Crossetta, Jr.; Arthur S. Cookfair

[57] ABSTRACT

Thianthrene compounds are prepared by adding sulfur monochloride to an excess of a benzene compound in the presence of aluminum chloride, and reacting to form a thianthrene compound as an insoluble aluminum chloride complex; slurrying the complex in an inert organic liquid; treating the slurry with a Lewis base, such as ammonia to free the thianthrene compound from the complex.

10 Claims, No Drawings

PROCESS FOR THE MANUFACTURE OF SUBSTITUTED THIANTHRENE BASED PRODUCTS

BACKGROUND OF THE INVENTION

This application is a continuation-in-part of U.S. Pat. application Ser. No. 521,108, filed Nov. 5, 1974, now U.S. Pat. No. 3,997,560, issued Dec. 14, 1976.

This invention relates to an improved process for the manufacture of thianthrene compounds. Thianthrene and substituted compounds are useful in a variety of chemical processes, for example, as chemical intermediates in the preparation of dyestuffs such as thianthrene vat dyes. In addition, various thianthrene compounds are useful plasticizers, pesticides, and flameproofing agents. Recently it has been found that thianthrene compounds having electron withdrawing substituents such as halogens, on the aromatic nuclei thereof are especially useful as components of catalyst systems for the directed nuclear chlorination of alkylbenzenes. Although thianthrene compounds have been known for many years, little effort has been directed toward the development of a process suitable for commercial manufacture.

One laboratory method for the preparation of thianthrene compounds comprises the reaction of a benzene compound with sulfur monochloride in the presence of aluminum chloride. The reaction product is a thianthrene compound-aluminum chloride complex. The thianthrene compound may then be recovered from the aluminum chloride complex by treatment with iced hydrochloric acid followed by steam distillation and washing with a suitable solvent.

It is an object of the present invention to provide a process for the production and recovery of thianthrene based products which is direct and simple and which is adaptable to large scale commercial operations. A further object is to provide a method whereby a high purity thianthrene product may be produced in high yields. A still further object is to provide an improved process for the recovery of thianthrene compounds from a thianthrene compound-aluminum chloride complex.

SUMMARY OF THE INVENTION

It has now been found that substituted thianthrene compounds may be prepared as follows: Sulfur monochloride is added, preferably with stirring, to a stoichiometric excess of a benzene compound, in the presence of aluminum chloride, and reacted to form a thianthrene compound-aluminum chloride complex. The resultant complex is then slurried in an inert organic liquid solvent for the thianthrene compound and the slurry is treated with a Lewis base to free the thianthrene compound from the complex and dissolve the thianthrene compound in the organic solvent.

In the process, it is preferred that sulfur monochloride be added to the benzene compound rather than the reverse, since the addition of the benzene compound to sulfur monochloride may result in the formation of undesirable polymeric sulfur products. Furthermore, the addition of the sulfur monochloride is made slowly to prevent excessively brisk evolution of hydrogen chloride gas. To provide a reaction medium of suitable consistency for agitation and transfer through piping systems and to provide sufficient solvent for by-product sulfur, diphenyl sulfides and reaction impurities it is important that a molar ratio of benzene compound to sulfur monochloride be maintained at about 5.0 or higher. Higher ratios may be employed with no theoretical upper limit. However, the process of the present invention becomes somewhat less economical when the mole ratio of benzene compound to sulfur monochloride is greater than about 12.0 due to the necessity of handling excessively large volumes of liquid. The preferred mole ratio of benzene compound to sulfur monochloride is between about 6.0 and 8.0.

The thianthrene compounds prepared in accordance with this invention are described hereinbelow in accordance with the current Chemical Abstracts system whereby the numbering of ring positions is as follows:

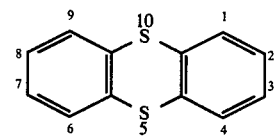

The amount of aluminum chloride present may vary considerably. However, we have found that maximum yields of thianthrene compound and minimum production of by-product substituted diphenyl sulfide are achieved when aluminum chloride is present in a mole ratio of aluminum chloride: sulfur monochloride of between about 0.4:1 and 1.6:1. At lower ratios the yield of thianthrene compound is substantially lowered. At higher ratios, the yield of thianthrene compound is lowered and the production of diphenyl sulfide is increased. The temperature of the reaction may vary considerably, for example, from about 20° Celsius to the boiling point of the benzene compound. Preferably, the reaction temperature is maintained at about 60° to about 160° Celsius. At lower temperatures, increased formation of undesirable diphenyl sulfides is likely to occur. The process is preferably carried out at atmospheric pressure, although subatmospheric and superatmospheric conditions may be employed, if desired, with appropriate adjustments in the upper temperature limit.

Upon completion of the reaction, the reaction vessel is cooled to room temperature and the contents filtered. The filtrate, consisting of benzene compound and unwanted reaction by-products and sulfur is removed and the remaining solids, a thianthrene compound-aluminum chloride complex, are slurried in an inert organic liquid, such as monochlorotoluene or benzene. A Lewis base, such as anhydrous ammonia is sparged through the slurry, preferably at a temperature of between about 25° and 65° C to break the insoluble thianthrene compound-aluminum chloride complex and separate the thianthrene compound in the soluble phase. The amount of Lewis base employed may vary considerably. Essentially complete separation, under the conditions shown may generally be accomplished with the addition of between about 0.3 and 0.5 parts by weight of ammonia per part of crude complex. Aluminum chloride and ammonia form insoluble complexes which are then filtered from the solution. The product thianthrene compound is then recovered in high yields by evaporation and crystallization of the liquor.

The thianthrenes which may be prepared in accordance with this invention are those characterized by the formula

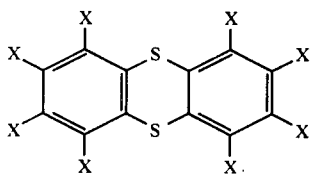

wherein each X is independently selected from the group consisting of hydrogen, methyl, ethyl, chlorine, bromine and fluorine. Most preferred are the di- and tetra-substituted thianthrenes wherein the substituents are selected from methyl and chlorine. Such compounds are prepared in the manner described from an appropriately selected benzene compound having at least two adjacent ring positions unsubstituted. The benzene compound starting materials are characterized by the formula

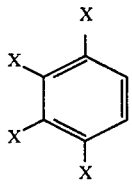

wherein each X is independently selected from the group consisting of hydrogen, methyl, ethyl, chlorine, bromine and fluorine. Most preferred are mono and di-substituted benzene compounds wherein the substituents are independently selected from methyl and chloride. Thus, the preferred substituted benzene compound starting materials include for example, toluene, orthochlorotoluene, parachlorotoluene, metachlorotoluene, paraxylene, orthoxylene, metaxylene. The particular thianthrene compound prepared will depend on the position of the substituents on the benzene ring, and in some instances may be a mixture of thianthrene compounds. Thus, for example, when paraxylene is employed as the starting material, the thianthrene compound product will be 1,4,6,9-tetramethylthianthrene. When the starting material is metaxylene, the product will be a mixture of the 1,3,6,8- and 1,3,7,9-isomers of tetramethylthianthrene.

Various Lewis bases may be employed in recovering the thianthrene compound from the thianthrene compound-aluminum chloride complex. Typical Lewis bases include for example, ammonia, pyridine, diethylamine and the like. Based on efficiency, cost and availability, the preferred Lewis base is ammonia. The organic solvent in which the thianthrene compound-aluminum chloride complex is slurried may be selected on the basis of three primary considerations. First, the solvent must be one in which the thianthrene compound is soluble. Second, the solvent must be substantially inert to ammonia or other Lewis base employed. In addition, the solvent must be one in which the thianthrene compound-aluminum chloride complex is substantially insoluble. Solvents suitable for this purpose include for example, benzene, monochlorobenzene, toluene, monochlorotoluene, tetrahydrofuran, carbon tetrachloride, chloroform, acetylene tetrachloride, perchloroethylene, trichloroethylene, xylene, and the like as well as mixtures thereof, and other organic solvents that meet the considerations set forth above. Optionally, all or a part of the solvent employed may be an excess of the benzene compound reactant. Thus, for example, in the preparation of dimethyldichloro thianthrene from sulfur monochloride and orthochlorotoluene in the presence of aluminum chloride, a stoichiometric excess of the orthochlorotoluene may be used and will serve as a solvent for the dimethyldichlorothianthrene when the latter is separated from the complex. Additional amounts of the same or other suitable solvent may be added.

The following examples will serve to further illustrate the invention and the manner in which it may be practiced. The examples are set forth for purposes of illustration and are not to be construed as limitative of the present invention. In the examples, unless otherwise stated, all parts and percentages are by weight and all temperatures are in degress Celsius.

EXAMPLE 1

Approximately 4080 parts of benzene was charged to a batch type stirred tank reactor together with 921 parts of aluminum chloride. The charge was heated to 60–70° C and while stirring, 710 parts of sulfur monochloride was fed dropwise into the reactor. The proportion of reactants provided a molar ratio of benzene to sulfur monochloride of about 10 and a molar ratio of aluminum chloride to sulfur monochloride of about 1.3. After sulfur monochloride addition, the resultant mix was refluxed for three hours at 75–80° C, cooled and filtered. A yield of 1272.4 parts of crude thianthrene:AlCl$_3$ complex was obtained.

One hundred parts of the crude thianthrene:AlCl$_3$ product was slurried in 500 parts of monochlorotoluene in a reaction vessel. The monochlorotoluene employed was a mixture of approximately 50% orthochlorotoluene and 50% parachlorotoluene. Anhydrous ammonia was sparged to the slurry with stirring. The rate of addition of ammonia was optimized by first sparging ammonia so that there was ammonia break-through in the reaction vessel followed immediately by cutting back of the rate so that there was no apparent bubbling in the reactor. Temperature was gradually increased and the rate of absorption of ammonia by the slurry by the above technique was recorded. It was found that at 60–62° C, the absorption rate was 0.1628 parts of NH$_3$ per 100 parts of slurry per minute. Increasing the ammonia rate showed bubbling in the reactor since the slurry can absorb ammonia only at a certain rate. The total ammonia thus sparged was 36.2 parts per 100 parts of crude.

The yield of high purity thianthrene (greater than 99.2% pure, melting at 151–155° C) was 21.07 parts, or 21.07% based on crude thianthrene:AlCl$_3$ complex. The residue was reslurried in 216.4 parts of monochlorotoluene and recovery by similar procedure was 4.82 parts of thianthrene, m.p. 149–153° C and 97.48% purity. An additional reslurring of the residue in 216.6 part of monochlorotoluene and reaction with ammonia resulted in the recovery of 1.47 parts thianthrene, having a melting point of m.p. 150–156° C, and a purity of 96.74%.

Thus it was found that a ratio of 1 part to 10 parts of crude to monochlorotoluene resulted in as nearly maximum extraction of thianthrene in the original crude filter cake, producing a net yield of 61.5% thianthrene based on sulfur monochloride as the limiting reactant.

EXAMPLE 2

Following the procedure of Example 1, 624 parts of benzene was charged to a batch type stirred tank reactor along with 90 parts of $AlCl_3$ and reacted with 108 parts of sulfur monochloride to yield 175.6 parts of crude thianthrene:$AlCl_3$ complex.

Fifty parts of the crude thianthrene:$AlCl_3$ complex was slurried in 500 parts of orthochlorotoluene and by similar ammonolysis treatment as described in Example 1 18.75 parts of thianthrene was obtained which gave a net yield of 76.2% based on $S_2Cl_2$ as the limiting reactant.

EXAMPLE 3

Twenty parts of a thianthrene:$AlCl_3$ complex was slurried in 200 parts of benzene and 20 parts of diethylamine was added slowly over a 20 minute period at a reaction temperature of about 50° C. The slurry was filtered. A portion of the filtrate was evaporated to dryness and found to contain 85.2 percent thianthrene. The final thianthrene product represented a yield of 66.4 percent based on the sulfur monochloride reactant.

EXAMPLE 4

The procedure of Example 3 was repeated except that in place of the diethylamine, 20 parts of pyridine was added followed by an additional 25 parts over a period of 55 minutes. The yield of thianthrene, based on sulfur monochloride reactant, was 58.6 percent.

EXAMPLE 5

A mixture of 126.5 parts of orthochlorotoluene and 13.35 parts of aluminum chloride was stirred and heated to about 40° C. Stirring was continued and the temperature maintained while 22.5 parts of sulfur monochloride was added slowly to the mixture over a period of about one half hour. After completion of the sulfur monochloride addition, the temperature of the reaction mixture was maintained at about 40° C. Ammonia was then bubbled slowly into the reaction mixture until the reaction mixture changed in color from a dark green-blue to a yellow. At this point 149 parts of chloroform was added and the addition of ammonia was continued until the reaction mixture was found to be alkaline to litmus paper. The mixture was filtered and washed with chloroform. Gas chromatographic analysis of the filtrate indicated a 56.6 percent yield of thianthrene product, based on sulfur monochloride, containing approximately 33 percent dimethylthianthrene, 23 percent dimethylmonochlorothianthrene, and 44 percent dimethyldichlorothianthrene.

What is claimed is:

1. The process for the manufacture of substituted thianthrene compounds wherein a substituted thianthrene compound is separated from a substituted thianthrene compound-aluminum chloride complex by admixing the complex with an inert organic liquid solvent for the substituted thianthrene compound to form a slurry therewith, and treating the slurry with a Lewis base to free the substituted thianthrene compound from the complex, and dissolving the substituted thianthrene compound in the organic liquid.

2. A process according to claim 1 wherein the Lewis base is ammonia.

3. A process according to claim 1 wherein the Lewis base is diethylamine.

4. A process according to claim 1 wherein the Lewis base is pyridine.

5. A process according to claim 1 where in the substituted thianthrene compound is dimethyldichlorothianthrene.

6. A process according to claim 5 wherein the Lewis base is ammonia.

7. A process according to claim 1 wherein the organic liquid solvent is monochlorotoluene.

8. A process according to claim 1 wherein the organic liquid solvent is chloroform.

9. A process according to claim 1 wherein the substituted thianthrene compound-aluminum chloride complex is prepared by adding sulfur monochloride to a benzene compound in the presence of aluminum chloride.

10. A process according to claim 9 wherein the benzene compound is orthochlorotoluene and the substituted thianthrene compound is dimethyldichlorothianthrene.

* * * * *